United States Patent [19]

Miglianico et al.

[11] Patent Number: 4,869,109
[45] Date of Patent: Sep. 26, 1989

[54] AUTOMATIC PROCESS FOR IDENTIFICATION OF DEFECTS BY ULTRASOUND AND CORRESPONDING SYSTEM

[76] Inventors: Thierry Miglianico, 4 rue Raie Tortue 91240, Saint-Michel-sur-Orge; Jean-Francois Mougel, 6, rue Rimbaud 91470, Limours; Francois Papezyk, 47, rue Molière 91470, Limours; Pierre Wident, 12, rue des Violettes 91600, Savigny sur Orge, all of France

[21] Appl. No.: 192,533

[22] Filed: May 11, 1988

[30] Foreign Application Priority Data

May 12, 1987 [FR] France ............................... 87 06658

[51] Int. Cl.⁴ .......................................... G01N 29/00
[52] U.S. Cl. ........................................ 73/602; 73/620
[58] Field of Search ................ 73/602, 606, 609, 618, 73/619, 620, 627; 382/19, 22, 36, 53; 367/13

[56] References Cited

U.S. PATENT DOCUMENTS

| 3,857,052 | 12/1974 | Beller | 367/13 |
|---|---|---|---|
| 4,312,229 | 2/1988 | Hurwitz et al. | 73/603 |
| 4,393,711 | 7/1983 | Lapides | 73/602 |
| 4,503,557 | 3/1985 | Maeda | 382/36 |
| 4,518,992 | 5/1985 | Kessler et al. | 358/112 |
| 4,524,622 | 6/1985 | Suzuki et al. | 73/620 |
| 4,531,409 | 7/1985 | Koch et al. | 73/602 |
| 4,658,372 | 4/1987 | Witkin | 382/36 |

FOREIGN PATENT DOCUMENTS 2361649 3/1978 France.

Primary Examiner—Michael J. Tokar
Assistant Examiner—Louis M. Arana
Attorney, Agent, or Firm—Nutter, McClennen & Fish

[57] ABSTRACT

In an automatic process and apparatus useful in the testing of welds, identification of a defect of a determined type in a part by ultrasound is accomplished in the following way:

an ultrasound image of the part is produced;

object points are created by extracting the contours of the existing regions of disjunction;

a list of objects of this filtered image is established, with each object defined geometrically by its contour;

for each object, the values are calculated for attributes of a predetermined list of attributes which characterize an object;

for each object, the attribute values are compared to minimal and/or maximal values determined in the course of a programming phase, using sample parts in which the defects of interest are present and identified by a specialist, and welding defects are identified as a function of the result of this comparison.

9 Claims, 5 Drawing Sheets

AUTOMATIC PROCESS FOR IDENTIFICATION OF DEFECTS BY ULTRASOUND AND CORRESPONDING SYSTEM

The present invention has as its object an automatic process for identification of defects by ultrasound. It has also as its object a corresponding apparatus.

The invention concerns the domain of non-destructive testing, and more particularly ultrasound testing of the quality of materials, and especially of welds. This testing is fundamental, from the viewpoint of reliability, in numerous technical domains such as pressure systems (steam boilers, petrochemical equipment, . . . ) or supporting materials (cranes, cable-railways, aircraft, . . . ).

Numerous processes are known for identification of welding defects by ultrasound, but each of these processes requires a human operator.

In a familiar system, a human operator moves a sensor, comprising an ultrasound emitter and ultrasound receptor, in proximity of the weld to be analyzed. Defects are identified as a function of the diminution of the ultrasound echo received by the receptor as the sensor is moved.

In this system, the operator has a certain amount of latitude in the choice of movements of the sensor, in the choice of the sensor itself, and the operator himself analyzes the form of the ultrasound echo. At the end of a stage of movement of the sensor, the operator communicates to the data system such information as the form of the ultrasound echo, the reflectivity differences obtained with various orientations, et cetera. The system then diagnoses any existing defects as a function of the data received.

It is thus observed that the system cannot function without the involvement of a human operator, and that the operator must be technically competent in order to be capable of supplying the correct data to the system.

Also known is a process of identification of weld defects consisting in a first stage of sweeping a weld with a probe, in order to produce an ultrasound image; this image is a point-by-point recording of the amplitude of the ultrasonic signal reflected by the weld. In a second stage, a specialist is called upon to interpret the ultrasound image to identify weld defects.

To facilitate the task of the specialist, the ultrasound image can be presented in the form of a map using false coloration. Each color corresponds to a particular amplitude range established in advance, and has no direct relationship whatsoever with the defects to be identified.

This process can be put into use only by a specialist.

In the known methods of identification of weld defects, it is necessary to take recourse to the judgment of a human operator either to deliver the data to an automatic processing system, or to identify the defects. This is clearly not satisfactory, because the quality of the analysis of the human operator can vary with time, for example as a function of external conditions (fatigue, etc.), and also because the number of tests which can be made is limited by reason of the small number of qualified specialists.

The invention thus has as its object to enable an automatic identification of defects, especially in a weld. This offers the advantages of a consistent quality of analysis, and the possibility of rapidly testing a large number of parts.

The process of the invention consists of producing, in familiar manner, an ultrasound image of the part, and then, in a characteristic manner, to automatically analyze that ultrasonic image to identify defects present in the part.

To be precise, the invention has as its object an automatic process for identification of defects by ultrasound, to identify a defect of a determined type in a part, with the said process comprising a first stage to produce an ultrasound image of the part, in which:

the said part is swept by at least one beam of ultrasonic waves;

the point-by-point amplitude of the reflected or diffracted ultrasonic signals is recorded;

an ultrasound image is constructed, whose signal amplitude at each point is proportional to the said recording; with the said process being characterized in that it comprises a second stage with a view to recognizing the presence of a defect, by analyzing the said ultrasound image, in which:

the ultrasound image is filtered to eliminate the signals whose amplitude is less than a determined threshold, this threshold being a function of the nature of the defect in question, and this filtering producing disjoint zones corresponding to the ultrasound reflectors;

the test objects are created by extracting the contours of these disjoint zones;

a list is formed of the objects of the said filtered image, with each object being geometrically defined by its contour;

for each object, the values of attributes of a predetermined list of attributes characterizing an object are calculated;

for each object, the values of the said attributes are compared to the minimal and/or maximal values determined in the course of a learning phase, on sample pieces in which the said defects are present, and identified by a specialist;

the defects are identified as a function of the results of this comparison.

The process may be applied to the detection of a single type of defect, or to the detection of a number of different types of defects. In the latter case, the different types of defects are sought simultaneously, by applying different thresholds to the ultrasound image.

The properties of objects are defined by the values of the attributes of the objects. These attributes can be of a geometric nature (position in the image, dimensions), or physical in nature (linked to the amplitude of the image points constituting the object).

The invention also has as its object an automatic system for identification of defects by ultrasound. This system comprises a first apparatus to produce, in classical fashion, an ultrasound image, and a second apparatus or system to identify defects by analyzing the said ultrasound image, according to the process of the invention.

In an advantageous fashion, the analysis mechanism comprises a controllable filtering apparatus to apply a threshold to the ultrasound image, an image-processing mechanism to seek the objects contained in the image subjected to the threshold, and a recognition mechanism, in the form of an expert system, composed of the list of objects, constituting the database of the expert system, the list of properties of the characteristic objects of each type of defect, this list constituting the knowledge base of the expert system, and processing means to interpret the objects of the database as a function of the knowledge base.

It can be seen that the first operation, which leads to the formation of artificial objects, not having an a priori relationship with the presence of a defect, has no equivalent in the familiar processes.

The justification for the process according to the invention rests on the experimentally obtained confirmation that in a surprising way, it is possible to associate with each type of defect at least one threshold value determined by filtering of the ultrasound image, and in the filtered and processed image, the presence of defects of the given defect type is characterized by objects having particular properties, especially particular geometric properties.

The characteristics and advantages of the invention will become clearer from the following description, given by way of non-limitational illustration, with reference to the appended drawings, in which:

FIG. 1 is an organization chart of the process of the invention;

FIG. 2 schematically illustrates a mode of realization of a system for implementation of the process of the invention;

Figure 1:
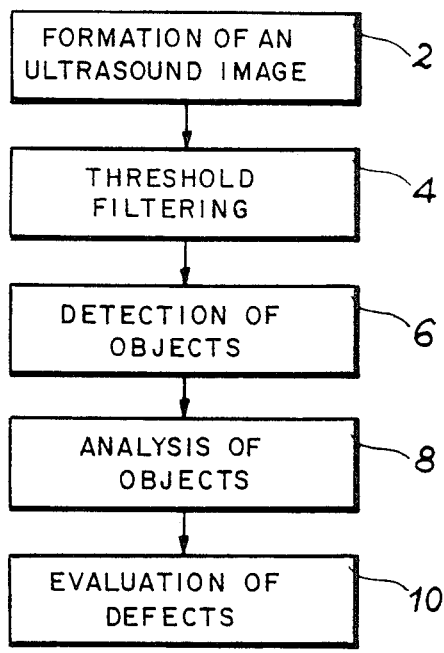

The process of the invention is constituted by a sequence of operations which are indicated in the organization chart of FIG. 1.

The initial operation 2 concerns the formation of an ultrasound image. The process of obtaining such an image is familiar. It consists of emitting in the direction of the weld to be analyzed at least one beam of ultrasound waves, and of recording the amplitude of the reflected or diffracted ultrasound waves. By displacement of the ultrasound beams with respect to the weld, the amplitude of the reflected or diffracted ultrasound waves is measured at a great number of points. In this way, an ultrasound image is constructed.

This ultrasound image may be unidimensional, bidimensional, or tridimensional.

A unidimensional image corresponds to the case in which the emitter of the ultrasound waves has only a single degree of freedom.

A bidimensional ultrasound image may be obtained in two ways. It can result from a displacement of the emitter along two non-parallel directions; the ultrasound image then represents a projection of the weld in the plane defined by the two directions. A bidimensional ultrasound image can also result from an emitter displaced along a single direction, with the other dimension being given by measurement of the depth at which the ultrasound beam is reflected within the weld. This depth is determined by the time elapsed between the emission of an ultrasound beam and the reception of the corresponding reflected or diffracted wave.

Finally, a tridimensional image may be obtained by combining the displacement of the emitter along two non-parallel directions, thus defining a plane, and a measurement of the depth at which the ultrasound wave is reflected, along the direction perpendicular to that plane.

The utilization of a tridimensional image is of interest in the case of thick parts (>1 cm), such as parts of composite materials utilized in aeronautics. In fact, it is necessary to be able in this case to localize a defect in depth with precision, and to define its volume.

As has been represented in FIG. 1, the operation 2 of formation of an ultrasound image is followed by an operation 4 of threshold filtering of this image.

The ultrasound image is filtered with a threshold whose level, conforming to the invention, is characteristic of the type of weld defect being sought. This operation has the effect of replacing amplitudes lower than the threshold with zero amplitudes.

The filtered image thus consists of zones where the image points have zero amplitudes, and zones where the image points have amplitudes greater than the threshold.

The operation 6 involves the automatic detection of zones where the image points have an amplitude greater than the threshold. These zones are termed "objects" in the terminology of the process of the invention. The localization of these objects is performed by so-called contour extraction techniques, which are entirely familiar in the area of computer image processing.

Operation 6 consists not only of localizing the objects in the filtered ultrasound image, but also of characterizing the objects, that is, of determining their properties.

This characterization takes the form of a set of values attached to attributes. These consist of attributes of a geometric nature, and attributes of a physical nature.

Without being exhaustive, it is possible to cite as attributes of a geometric nature:

the position of the object in the image, the dimension of the object; and as attributes of a physical nature:

the mass of the object, that is, the sum of the amplitudes of the image points making up the object, the density of the object, that is, the ratio of its mass to its area, the position of the center of gravity corresponding to the object, the maximum amplitude, the position of the signal of maximum amplitude.

When the objects contained in the filtered ultrasound image are localized and characterized, that is, they have been individualized by determination of the series of values of their attributes, according to the organization chart of FIG. 1, the process proceeds to an analysis of the objects to identify the defects of the type sought.

This operation of analysis 8 is an operation of identification of objects according to a logical process utilizing predetermined operational limits of these attributes. An object is recognized as representative of a defect if the set of its parameters:

verifies the rules derived from experimental knowledge, fulfills the conditions linked to the properties of the attributes, fulfills or fails to fulfill the necessary conditions of association.

The operational limits are defined in the course of a learning operation, during which ultrasound images are produced of sample welds presenting a determined type of defect, these ultrasound images are filtered according to a threshold suited to the type of defect, and in the objects representing a defect, one seeks to define the characteristic and determinant parameters (attributes and attribute values) indicating presence of the defect.

Further description will be given below, with reference to FIG. 4, of a means of implementation of the operation of analysis 8 constituted by an expert system.

The final operation constituting the process of the invention is an operation 10 of evaluation of defects, as represented in FIG. 1. This evaluation, which results in acceptance or rejection of the welded part, is based on selective criteria validated by experience and comparative destructive tests, and the specification in effect.

The process of the invention which has just been described with reference to FIG. 1 is an automatic process of identification. No human operator intervenes in the testing of a weld and the interpretation of the results, which enables avoidance of errors of judgment of human origin, caused, for example, by fatigue.

Figure 2:
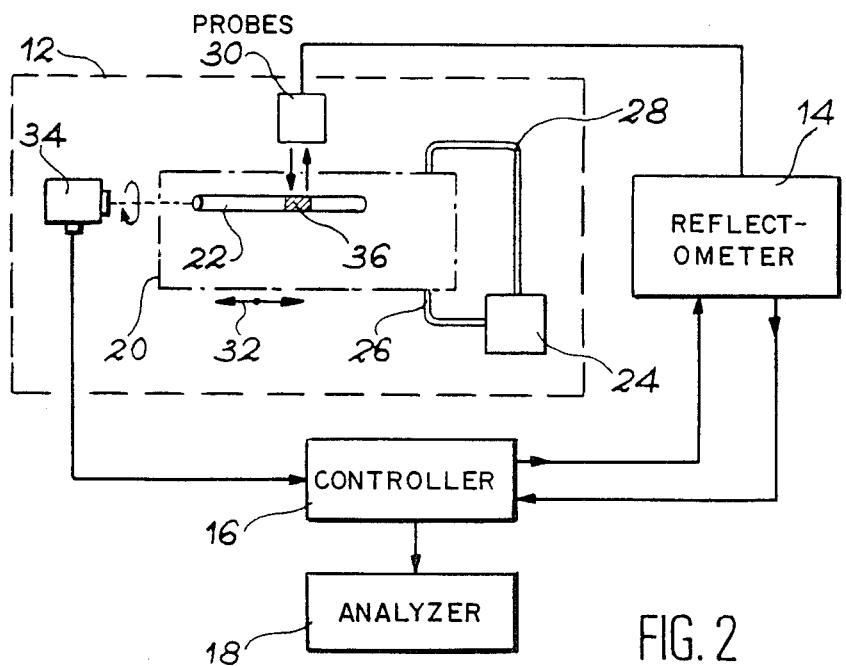

The process of the invention is thus implemented by an automatic processing system. FIG. 2 illustrates schematically one mode of embodiment of this system.

It comprIses a measurement bench 12, a reflectometer 14, a control apparatus 16, and an analysis apparatus 18.

The measurement bench 12 comprises a tank 20, into which is placed the welded part 22 to be analyzed. The tank 20 is filled with water so as to ensure constant coupling of the ultrasound energy between the probe and the part to be tested. In this case, circulation of the water is provided by means of a pump 24 which receives water from the base of the tank through a channel 26, and expels it at the top of the tank through a channel 28.

The measurement bench 12 also includes a probe 30 comprising an emittor-receptor of ultrasound waves. In the schematic representation of FIG. 2, a single probe is represented; however, in practice, two or three probes are utilized, which emit ultrasound waves with different angles of incidence.

The measurement bench 12 includes, lastly, means of displacement of the welded part 22 with respect to the probe(s). In general, the tank and the probes are stationary with respect to one another. The part to be tested is turned, while the tank and the probes are displaced longitudinally. The scan is helicoidal. The displacement mechanisms depend on the ultrasound image which one desires to obtain, and the shape of the weld to be analyzed.

By way of example, the displacement mechanisms may consist of a means of translation of the tank, represented schematically by a double arrow 32 in the figure, and a means of rotation 34 of the part 22, in the case in which the weld forms a ring 36 around a cylindrical piece.

The reflectometer 14 ensures the generation of ultrasound waves by supplying the emitters of the probes 30, and the reception of the detected ultrasound echos.

The ultrasound waves utilized in nondestructive testing have a frequency on the order of 100 khz to several megahertz. In the present application, the ultrasound waves have for example a frequency between 1 and 10 Mhz.

It is known that the use of a high frequency increases the sensitivity of measurement, but on the other hand increases the attenuation of the wave, which diminishes the maximum depth of penetration which may be achieved. The choice of frequency thus results from a compromise which depends upon the welded part to be analyzed and the type of defect being sought.

The ultrasound image is constructed point by point. In the case represented in FIG. 2, the ultrasound image may be bidimensional, with one coordinate axis corresponding to translation displacement of the tank operated by the mechanism 32, and the other coordinate axis corresponding to the angular displacement of the part operated by the mechanism 34. The image may also be tridimensional, if in addition the measurement of the ultrasound echo delay with respect to the emitted wave is sufficiently precise to be able t determine the depth at which the reflection has occurred.

Figure 3:
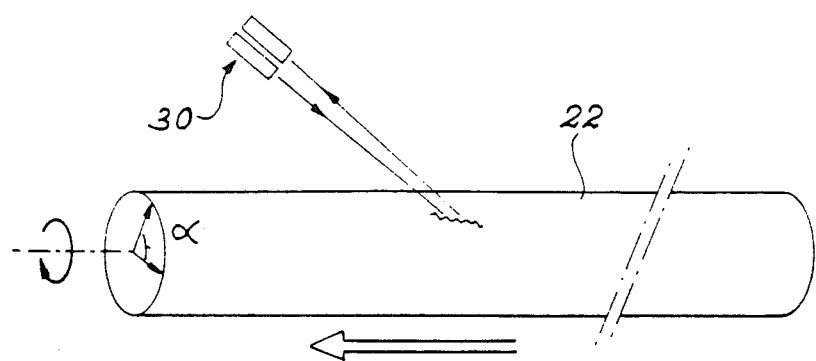
FIG. 3 illustrates the principle of measurement by ultrasound.

The principle of ultrasound measurement is represented in FIG. 3. The part 22 is placed in rotation around its axis while the tank is displaced in translation parallel to the axis of the part. For each emission of an ultrasound wave, the angular and longitudinal coordinates of the part are recorded, which determines the position of impact of the ultrasound wave. The amplitude of the ultrasound echo is registered by the reflectometer 14, with this echo detection being possible only during a predetermined time interval after emission of the ultrasound wave, to avoid detection of parasitic echos.

The measurement is repeated for a large number of points, and the result is presented in the form of an image on a screen.

The reflectometer 14 constructing the ultrasound image can be for example an instrument of the type of an S80 reflectoscope of Automatisation Internationale.

The ultrasound image is delivered, possibly in digital form, to the control apparatus 16. This unit controls actuation of the displacement mechanisms 32, 34, and of the reflectometer 14.

This control apparatus is by preference a computer having means to store the ultrasound image, means for display and printing of this ultrasound image, and means to communicate with a human operator in order to be able to define the measurement to be performed, by specifying the amplitude and the velocity of displacements of the welded part to be analyzed, the number of probes used, the angle of incidence of the ultrasound waves emitted by the probes, the temporal window during which the reflectometer is active to detect an ultrasound echo, and in a general manner to fix the value of all the parameters intervening in the measurement.

The control apparatus can be implemented, for example, by an INTEL 86310 microcomputer of the INTEL corporation, and the associated peripheral devices.

The system represented in FIG. 2 comPrises a measurement bench 12, a reflectometer 14 and control apparatus 16 which are combined in classical fashion to produce an ultrasound image of a weld.

This system furthermore comprises an analytical apparatus 18 which enables automatic identification of a defect from the ultrasound image. This analytical apparatus implements the essential operations of the process of the invention.

Figure 4:
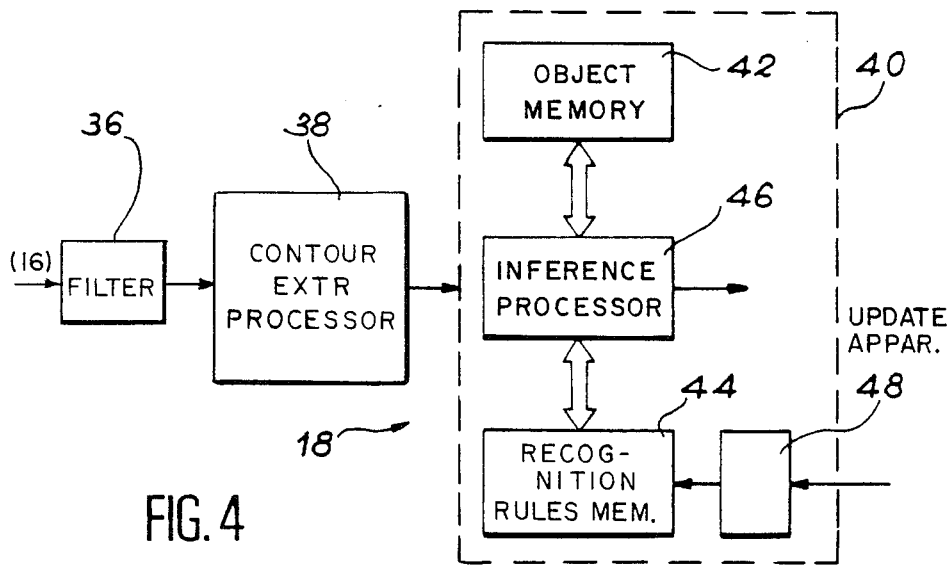
FIG. 4 represents schematically a mode of realization of the analysis mechanism of the system according to the invention.

One particular mode of embodiment of this analytical apparatus is represented in FIG. 4. It includes three elements: a filtering mechanism 36, a processing mechanism 38 and a recognition mechanism 40.

The filtering mechanism 36 receives the ultrasound image from the control apparatus 16. Conformant to the invention, it carries out a threshold filtering on this image, with the threshold defined as a function of the type of defect sought. The level of the threshold can be determined in the course of a preceding learning phase, in an experimental manner, by analyzing sample welds presenting the type of defect sought.

The threshold filtering has as its effect to replace with a zero amplitude the amplitudes of points of the image which are less than the threshold. The filtered image thus consists of zones where the points have an amplitude greater than the threshold in a background consisting of points with zero amplitude.

The components of the image termed objects are the basis for the recognition of defects, in the process according to the invention.

These objects are localized by the processing apparatus 38 which performs a classical image processing of the contour extraction type. This treatment enables the objects to be geometrically delimited.

The treatment is supplemented by an identification of the objects, that is, by the determination, for each object, of attribute values of a predetermined list of attributes. As indicated above, this list of attributes can include attributes of a geometric nature, such as the position of the object in the image or the size of the object, and attributes of a physical nature, such as the mass or density of the object.

The identified objects are then transmitted to the recognition apparatus 40, for which they constitute the base data for the identification of weld defects. This identification is carried out according to the principles previously outlined in the description of the process (description of the analysis operation 8).

The recognition apparatus 40 represented in FIG. 4 implements this method of recognition. It is presented in the form of an expert system, that is, an automatic recognition system modelling the behavior of a human expert.

The recognition apparatus 40 comprises:

a first memory 42 to receive the list of objects of the filtered image, which memory constitutes the database of the expert system, a second memory 44, to store the knowledge of a human expert in the form of a set of rules, which memory constitutes the knowledge base of the expert system for recognition, a processing apparatus 46 to interpret the objects of the database as a function of the rules of the knowledge base, which processing apparatus constitutes the inference engine of the expert system, an updating apparatus 48 to modify the knowledge base as a function of the type of defect sought.

The process of identification implemented by the recognition apparatus depends upon the weld to be analyzed and the types of defects sought. The operation of the recognition apparatus will be explained in a specific example.

It is known that in nuclear reactors, tens of thousands of fuel rods are implanted in the core. These rods are constituted by a sheathing tube enclosing the fuel material (uranium oxide), and are closed at their ends by two welded caps which ensure hermetic sealing.

Figure 5:
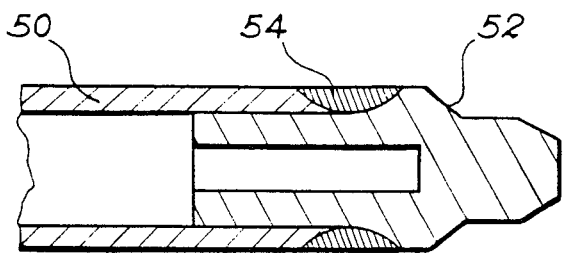
FIG. 5 is a cutaway view of one end of a fuel rod, with a weld to attach a cap to a casing.

A cutaway view of one end of a fuel rod is represented in FIG. 5. The casing 50 has a thickness of the order of 0.6 mm and a diameter on the order of 10 mm. A cap 52 is fixed to the end of the sheath by an annular weld 54.

An ultrasound image of the weld is produced by means of the system described in reference to FIG. 2. Taking into account the small thickness of the weld, it is not necessary here to establish a tridimensional ultrasound image. A plane image is sufficient; its coordinate axes comprise a longitudinal coordinate (abscissa x along the axis of the sheath) and an angular coordinate (angle $\alpha$ between 0 and 359°). These coordinates are supplied by position encoders associated with the displacement mechanisms 32, 34 of the system of FIG. 2. The ultrasound image includes 256 points per revolution, for example, (angular coordinate) with a step of 0.22 mm along the axis of the sheathing tube.

Three types of defects are sought in the ultrasound image: a porosity, a lack of penetration, and a collapsing of the sheath.

A preliminary study made on sample welds presenting each of these three types of defects made it possible to distinguish the characteristics of the ultrasound images associated with each type of defect.

This study showed that:

a porosity appears in the form of an object of small size, and generally with great density;

a lack of penetration can extend over the entirety of the weld; it is characterized by the presence of numerous separate but neighboring objects;

a collapse of the sheath appears in the form of a very fragmented object, of large area and high density.

Figure 6:
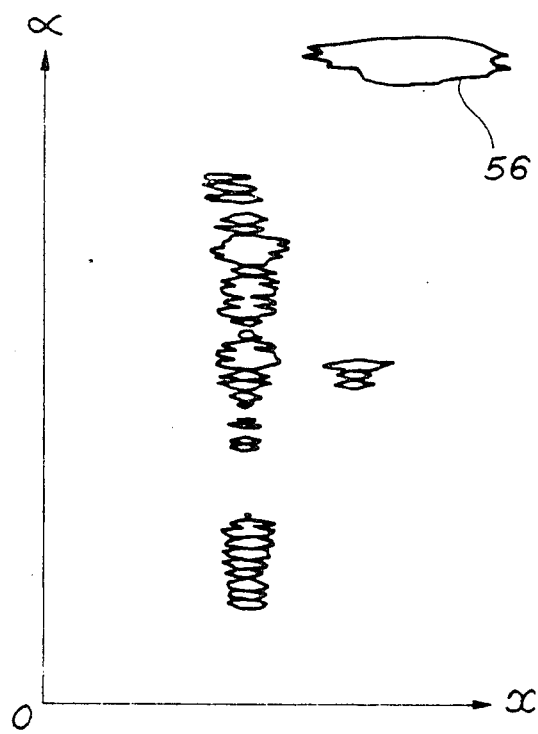
FIG. 6 represents a threshold filtered ultrasound image including an object characteristic of porosity of the weld.
Figure 7:
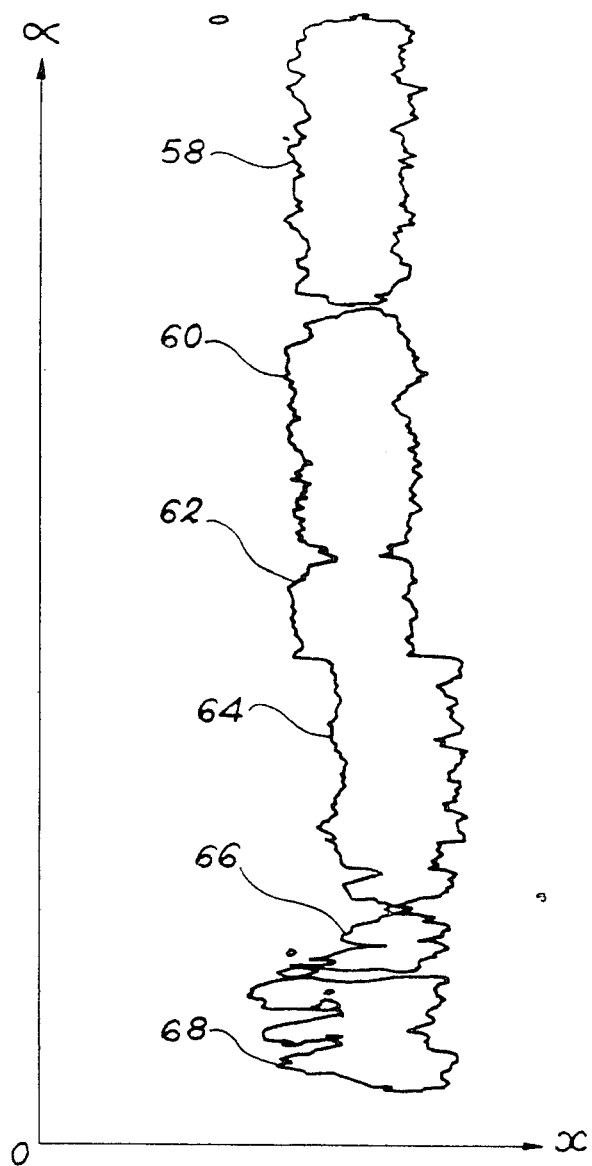
FIG. 7 represents a threshold filtered ultrasound image including an object which is characteristic of a lack of penetration of the weld.
Figure 8:
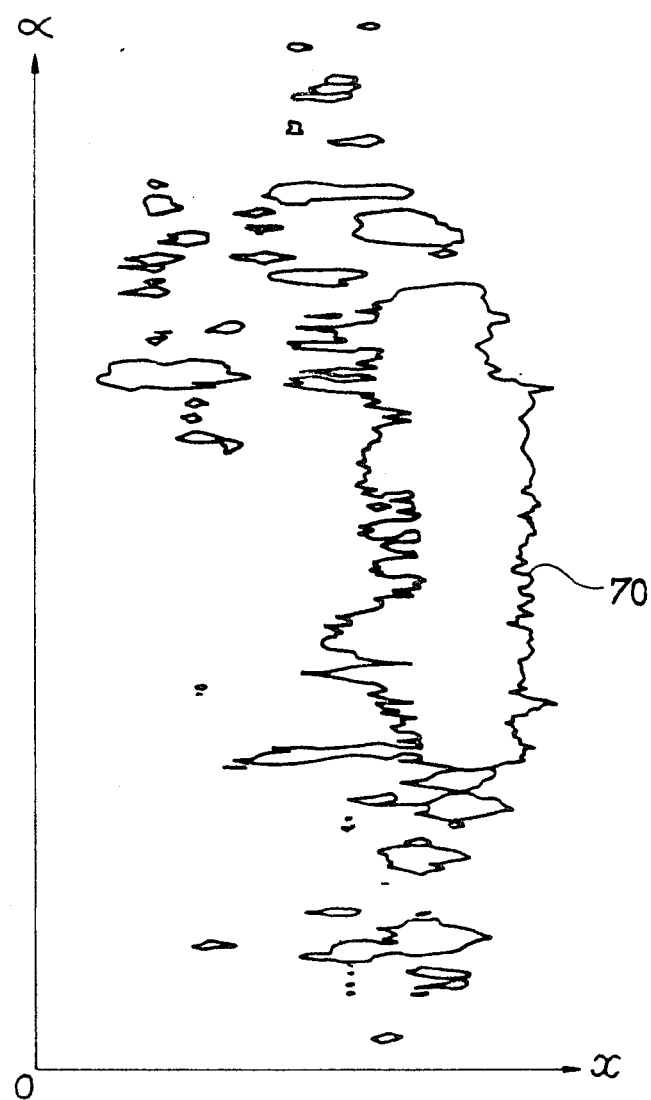
FIG. 8 represents a threshold filtered ultrasound image including an object characteristic of an internal collapse of the casing.

The graphic representations of FIGS. 6, 7 and 8 display respectively a porosity, alack of penetration, and a collapsing of the sheath. The outline, in heavy line, corresponds to the threshold applied to the image. (This threshold is different for the three representations, since the defects sought are of different types.)

In FIG. 6, the numeric reference 56 designates an object which is characteristic of the presence of a porosity. Similarly, the objects 58–68 of FIG. 7 are representative, by their number and proximity, of a lack of penetration of the weld. Finally, the object 70 of FIG. 8 is an object of large dimensions which indicates a collapse of the sheath.

For the recognition of the defects in the weld of the fuel rod of FIG. 5, the objects detected in the ultrasound image are characterized by the following attributes:

dimension of the object: longitudinal extension and angular extension (perhaps thickness, if the image is tridimensional);

localization of the object: longitudinal abscissa initially and longitudinal abscissa finally (perhaps depth, under the same condition);

perimeter, surface (and perhaps volume) of the object, expressed as a number of image points;

mass and density of the object, that is respectively, sum of the amplitudes of image points constituting the object, and ratio of that mass to the area;

maximum amplitude;

position of the center of gravity of the object.

The list of objects and the values of attributes are stored in the memory 42.

In the memory 44 are stored the knowledge enabling the recognition apparatus 40 to identify the defects. The knowledge is expressed in the form of rules, and includes rules established on the basis of the knowledge and rules established from the properties of the attributes.

The rules established on the basis of knowledge have the goal of determining:

the probe to be utilized in the case of a system which includes different probes (frequency of the ultrasound wave, angle of incidence of the wave with respect to the welded part, . . . ). In the application described, probes 30 in FIG. 2 include a probe PO is utilized for the detection of porosities, and two probes P1 and P2 for the detection of internal collapses of the sheath;

the filtering threshold of the ultrasound image. This parameter alters the number and form of objects contained in the image. It is determinant for analysis according to the type of defect sought.

The rules established on the basis of the properties of the attributes relate to:

the perimeter and area of objects. Minimum values are indicated, which enables elimination of small objects without significance;

the abscissa of the center of gravity. Minimum and maximum values are indicated for each type of defect;

the density. A criterion of minimum density and a criterion of maximum density fluctuation are utilized, to determine if two objects are of the same nature;

the interconnection of objects. This rule is developed for the recognition of a lack of penetration. It enables the recognition apparatus to confirm that the objects are proximate, which characterizes a lack of penetration, if the objects are of the same nature.

For the recognition of each type of defect, the rules are applied in an order determined by the inference engine. The search for defects is performed in the following order: porosity, lack of penetration, and then collapse of the sheath.

For the search for porosity, the following general rules are verified in succession:

abscissa of the center of gravity greater than a minimum value MIN1, abscissa of the center of gravity less than a maximum value MAX1, initial abscissa greater than a minimum value MIN2, initial abscissa less than a maximum value MAX2, longitudinal extension greater than a minimum value MIN3, longitudinal extension less than a maximum value MAX3.

If each of these rules is verified for an object, particular rules are verified to specify the category of the defect. Categories of porosity corresponding to porosities of different sizes can thus be defined. A set of specific rules, fixing particular values of attributes for each category of defects, is thus constructed. This set comprises the following rules:

value threshold S1, density greater than a minimum value D1, angular extension greater than a minimum value EMIN1, angular extension less than a maximum value EMAX1, maximum amplitude greater than a minimum value A1.

The set of values S1, D1, EMIN1, EMAX1, A1 defines a category of porosities. In the same manner, the values S2, D2, EMIN2, EMAX2, A2 define another category of porosities.

The identification of porosities is followed by identification of a lack of penetration. For this, the initial ultrasound image is taken again, and filtered according to a specific threshold value.

It is then verified whether the general rules, cited above, are satisfied. (The values of the attributes are different for the search for porosities and the search for lack of penetration.) If this is the case, the object is designated a candidate, and the weld may present a lack of penetration defect. The identification is made by verifying whether the following specific rules are satisfied:

area greater than a minimum value S, density greater than a minimum value D, distance between candidate objects less than a minimum value d, density fluctuation greater than a minimum value FD, total angular extension of contiguous objects greater than a minimum value EAT.

One then proceeds to the search for defects of collapse of the sheath, by filtering the initial ultrasound image with a specific threshold value.

In a first stage, it is verified that the general rules are satisfied. In these general rules, the values of attributes are specific to the type of defect sought.

If the result is positive, it is then verified whether the following specific rules are satisfied:

density greater than a minimum value DA, angular extension greater than a minimum value EMINA, angular extension less than a maximum value EMAXA, amplitude greater than a minimum value SS.

The process of reasoning implemented by the recognition apparatus leads to a quality of analysis which sometimes proves superior to and more rigorous than that of a human expert.

The system of identification described makes it possible to identify the three types of defects indicated in about 30 seconds.

The system presents the following advantages:

immediate analysis of the results, immediate decision of acceptance or rejection, adjustable selection parameters, high examination rate of 2000 welds per day, elimination of human errors of interpretation, dynamic monitoring of manufacture and its trends.

We claim:

1. An automatic process for the identification by ultrasound of a defect of a determined type in a part, said process comprising the steps of producing an ultrasound image of said part by sweeping the part with at least one beam of ultrasound waves, recording point-by-point the amplitude of the reflected or diffracted ultrasound wave for each point to produce a corresponding recorded value for that point, constructing an ultrasound image for which the amplitude of the signal at each point is proportional to said recorded value for that point; and analyzing said ultrasound image to recognize the presence of said defect by filtering said ultrasound image to eliminate signals whose amplitude is less than a determined threshold, said threshold being a function of the nature of said defect, thereby producing disjoint zones corresponding to ultrasound reflectors, extracting the contours of said disjoint zones to create objects, establishing a list of objects of said filtered image with each object being defined geometrically by its contour, characterizing each object by determining for each object, attribute values of a predetermined list of attributes characterizing an object, comparing for each object, the determined values of said attributes to minimum and/or maximum values determined in the course of a learning phase on sample parts in which said defect is present and identified by a specialist, so as to identify the defect in the part.

2. The automatic process according to claim 1 and further including one or more additional analyzing steps with each additional analyzing step being associated with a particular defect type, with the filtering threshold and the minimum and/or maximum values of said attributes for each step being a function of the type of defect being analyzed during that step.

3. The automatic process according to claim 1, in which the list of attributes includes at least one attribute of a geometric nature selected from the group consisting of the position of the object along at least one coordinate axis of the filtered ultrasound image, the dimension of the object along at least one coordinate axis of the filtered ultrasound image, and the ratio of the dimensions of the object along two coordinate axes of the filtered ultrasound image.

4. The automatic process according to claim 1 in which the list of attributes includes at least one attribute of a physical nature, selected from the group consisting of the mass of the object, equal to the sum of the amplitudes of the image points of the object.

the density of the object, equal to the ratio of its mass to its area, the maximum amplitude, equal to the greatest of the amplitudes of the signals at each image point of the object, and the position of the corresponding center of gravity of the object.

5. The automatic process according to claim 1 in which a criterion of proximity of said objects is used to identify a lack of penetration of a weld in said part.

6. The automatic process according to claim 2 in which first porosity and then lack of penetration is sought in a weld.

7. The automatic process according to claim 1 in which searches for defects are pursued in the following order: porosity, lack of penetration and collapse in order to identify a collapse of a welded part.

8. An automatic process for the identification by ultrasound of a defect of a determined type in a part according to claim 1, said process including a system comprising:

a measurement bench comprising at least one probe, with each probe being composed of an emitter of an ultrasound wave and a receptor of an ultrasound wave, and a means of displacement to move the probes with respect to said part, a reflectometer to generate ultrasound wave signals, receive the detected echoes, and construct a corresponding ultrasound image, a control apparatus to control said measurement bench and said reflectometer a filtering apparatus receiving the ultrasound image and applying a threshold to the said image, with said threshold being a function of the type of defect sought, a processing apparatus to carry out an extraction of contour within said filtered image, with this processing revealing objects constituted by image zones whose amplitude is greater than said threshold, and a recognition apparatus to identify the defects of said defect type as a function of said objects.

9. The system according to claim 8, in which the recognition apparatus comprises:

a memory to store the list of objects delivered by the processing apparatus, a memory to store the properties of objects associated with said type of defect, and a processing apparatus to recognize defects of said defect type by identifying the properties of the objects contained in the memory with the properties stored in the memory.

* * * * *